United States Patent

Tingey et al.

Patent Number: 5,807,605
Date of Patent: Sep. 15, 1998

[54] LUBRICANT SOLUBLE FLUORESCENT AGENT AND METHOD FOR ITS USE IN A SYSTEM FOR DETECTION OF LUBRICANT COATINGS

[75] Inventors: Kevin G. Tingey, Sandy, Utah; Victor A. Williamitis, Dayton; Charles W. Daugherty, Jamestown, both of Ohio; Jeanne E. Lambert, Conyers, Ga.; Steven H. Mersch, Germantown, Ohio

[73] Assignee: Becton Dickinson and Company, Franklin Lakes, N.J.

[21] Appl. No.: 840,484

[22] Filed: Apr. 21, 1997

Related U.S. Application Data

[62] Division of Ser. No. 606,718, Feb. 27, 1996, Pat. No. 5,667,840.

[51] Int. Cl.$^6$ .............................. G01N 21/64; G01J 1/42; B07C 5/34
[52] U.S. Cl. .............................. 427/8; 118/713; 209/578; 250/302; 250/372; 250/223 R; 250/461.1; 356/237
[58] Field of Search .................................. 250/302, 372, 250/461.1, 375, 304, 223 R; 427/8; 118/713, 500; 209/577, 578; 356/237

[56] References Cited

U.S. PATENT DOCUMENTS

| | | | |
|---|---|---|---|
| 3,527,709 | 9/1970 | Alburger | 252/301.2 |
| 3,721,501 | 3/1973 | Atkinson et al. | 356/201 |
| 4,250,382 | 2/1981 | Libby | 250/302 |
| 4,814,198 | 3/1989 | Baecklund | 427/9 |
| 5,001,353 | 3/1991 | Odake et al. | 250/461.1 |
| 5,047,444 | 9/1991 | DeVoe et al. | 522/99 |
| 5,087,684 | 2/1992 | Perrin | 528/22 |
| 5,102,461 | 4/1992 | Rheinberger et al. | 106/35 |
| 5,191,803 | 3/1993 | Gamache | 73/865.8 |
| 5,207,293 | 5/1993 | Eden et al. | 184/101 |
| 5,225,675 | 7/1993 | O'Donnell | 250/302 |
| 5,266,359 | 11/1993 | Spielvogel | 427/388.4 |
| 5,270,116 | 12/1993 | Melancon et al. | 428/447 |
| 5,354,825 | 10/1994 | Klainer et al. | 526/268 |
| 5,480,723 | 1/1996 | Klainer et al. | 428/441 |
| 5,545,830 | 8/1996 | Ziemelis et al. | 528/15 |
| 5,556,663 | 9/1996 | Chang et al. | 427/8 |
| 5,606,171 | 2/1997 | Neckers et al. | 250/459.1 |

FOREIGN PATENT DOCUMENTS 29 07 620 A1  8/1980  Germany.

*Primary Examiner*—Diana Dudash
*Attorney, Agent, or Firm*—Eric M. Lee

[57] ABSTRACT

A method for visualization of a lubricant coating on a surface of an article includes dissolving a fluorescent agent into a lubricant. The method then includes applying the fluorescenated lubricant to coat a surface of the article. The coated article is then irradiated with an electromagnetic radiation capable of inducing a fluorescent emission in the fluorescent agent and the fluorescent emission is observed to detect the coverage of the lubricant on the surface of the article.

4 Claims, 3 Drawing Sheets

LUBRICANT SOLUBLE FLUORESCENT AGENT AND METHOD FOR ITS USE IN A SYSTEM FOR DETECTION OF LUBRICANT COATINGS

This is a division of application Ser. No. 08/606,718, filed Feb. 27, 1996, now U.S. Pat. No. 5,667,840.

FIELD OF INVENTION

The present invention generally relates to the coating of objects and more particularly to materials, a method and a system useful for visualization of a lubricant coating on the surface of medical devices.

BACKGROUND OF THE INVENTION

Medical devices are often assembled from components formed from many different materials. It often is necessary to apply a coating of a lubricant to one or more of the components so that a component of one material will readily slide against a component of another material. Examples of this type of application are catheters with guidewires, over-the-needle catheters, syringe plunger stoppers within syringe barrels, needles for penetration of blood collection tube stoppers and the like. In other medical device applications, a lubricant is applied to a device to ease its penetration into the body. Examples of these applications are surgical blades, hypodermic needles, peripheral venous catheters and the like.

In all of these medical device lubrication applications, there are strict requirements on the amounts of lubricant, the uniformity of the application and a need to avoid contamination of the device with foreign material other than the lubricant. A further requirement on application of lubricant results from the high volume production requirements often resulting in the use of high speed assembly equipment. Thus, any lubricant application must be precise and compatible with high volume production.

Currently, a commonly used lubricant for medical devices is "silicone," i.e., polydimethylsiloxane having a Brookfield viscosity between about 1,000 and 1,000,000 centistokes (cs). For some applications, the silicone is applied "neat," i.e., without solvent. An example of neat application of silicone to syringe plunger stoppers is disclosed in U.S. Pat. No. 5,207,293 to Eden et al. This patent discloses a method and apparatus for lubricating syringe stoppers by moving the stoppers between a pair of wheels that are positioned partially in a reservoir containing lubricant so that, with rotation of the wheels, lubricant is transferred to the stoppers.

Another commonly used neat application method is tumbling a measured quantity of small parts, such as stoppers, with a measured quantity of lubricant so that the parts acquire a coating of the lubricant.

Silicone lubricant also may be sprayed onto the parts either neat or in a carrier solvent. Neat spraying has been found to work well for interior surfaces such as inside syringe barrels. Solvent based dipping or spraying is commonly used for coating hypodermic needles and percutaneous catheters. Chlorofluorcarbon solvents have proven to be very satisfactory for the delivery of silicone onto medical devices because they are non-toxic, non-flammable, inert, evaporate rapidly without leaving residue and are available in very high purity. Unfortunately, because of the belief that chlorofluorocarbon solvents are responsible for destruction of ozone in the upper atmosphere, most commonly used chlorofluorocarbon solvents will no longer be available. Alternate solvents such as hydrocarbons are flammable, and aqueous based systems generally are not practical for silicones.

When silicone lubricant is applied to a device in a solvent, the device is generally sprayed with or dipped in a dilute solution of the silicone containing solvent. In these application techniques, the solution with a low concentration of lubricant is generally present in excess. The dilute solution is often sprayed or flowed over the device being coated, in excess of the amount required to coat it. Thus, as long as this excess is maintained and monitored, there is substantial confidence that the medical devices have a substantially uniform coating of at least the minimum desired quantity. When the silicone is applied directly or "neat," there is not the same level of confidence that the desired amount of silicone is being applied. The actual amount of silicone lubricant applied to each individual device, such as an intravenous catheter or hypodermic needle is very small.

Two recent United States Patent Applications, commonly assigned with the present application, Ser. Nos. 08/509,393 and 08/509,395, disclose the neat application of polydimethylsiloxane to medical devices. An example given the in these referenced disclosures is the application of 12,500 cs. polydimethylsiloxane to 14 gauge intravenous catheters. In the examples, the referenced applications disclose that about 0.3±0.075 mg is applied to each individual catheter. Polydimethylsiloxane is a clear water white liquid. It is available in a wide range of viscosities ranging from about 50 cs. to about 1,000,000 cs. Because of the physical characteristics of polydimethylsiloxane and the small amount applied to each catheter, it is difficult to differentiate between a lubricated catheter and an unlubricated catheter by visual comparison. Thus, it is almost impossible to determine visually and rapidly if an individual catheter has the desired uniform coating. Since these catheters are medical devices, they must be manufactured according to Good Manufacturing Practices (GMP) as defined by the Food and Drug Administration. An important aspect of GMP is developing the ability to validate and to monitor production processes.

One way to determine the amount of silicone on a catheter is to carefully weigh identified catheters, feed them through the process and then reweigh them to determine the silicone loading. This technique allows a determination of the gross amount of polydimethylsiloxane on an individual catheter, but it is considered a "destructive" test, i. e., the identified catheter generally cannot be put back into the process. Additionally, with weighing, no determination can be made of the uniformity of the application. Another destructive method involves washing the polydimethylsiloxane off the catheter with a solvent, evaporating the solvent and weighing the residual polydimethylsiloxane. Again, washing does not address the need to determine if the application is uniform.

Because of the GMP requirements that the production of medical devices be validated and controlled, there is a need for a non-destructive method to monitor the application of lubricants to their surfaces. Additionally, since many medical devices are single-use and produced in large volumes, if the monitoring method was relatively inexpensive and compatible with high volume, high speed manufacturing processes, an additional benefit to the art of medical device manufacture would be realized. Materials, a method and a system for visualization of polydimethylsiloxane on the surface of a medical device are disclosed below.

SUMMARY

A method of the present invention for visualization of a polydimethylsiloxane coating on a surface of a medical device includes dissolving a fluorescent agent into a polydimethylsiloxane lubricant and applying the fluorescenated polydimethylsiloxane lubricant to the surface of the medical device. The method includes irradiating the surface with the lubricant with an electromagnetic radiation capable of inducing a fluorescent emission in the fluorescent agent. The method further includes detecting the fluorescent emission to thereby determine the degree of coverage of the polydimethylsiloxane on the surface of the medical device.

The method of the invention allows non-destructive visualization of small quantities applied in thin layers of polydimethylsiloxane lubricant for confirming its presence on the surface of small medical devices such as catheters, hypodermic needles and the like. Additionally, the method further allows non-destructive evaluation of the degree or uniformity of coverage of the surface of the device. A system that utilizes the method of the invention includes a source of electromagnetic radiation capable of inducing a fluorescent emission in polydimethylsiloxane having a fluorescing agent and a detector for detecting the emission. The system of the invention may be easily incorporated into an assembly line and used for monitoring large numbers of medical devices at a rate comparable to the rate of assembly.

DETAILED DESCRIPTION

Figure 1:
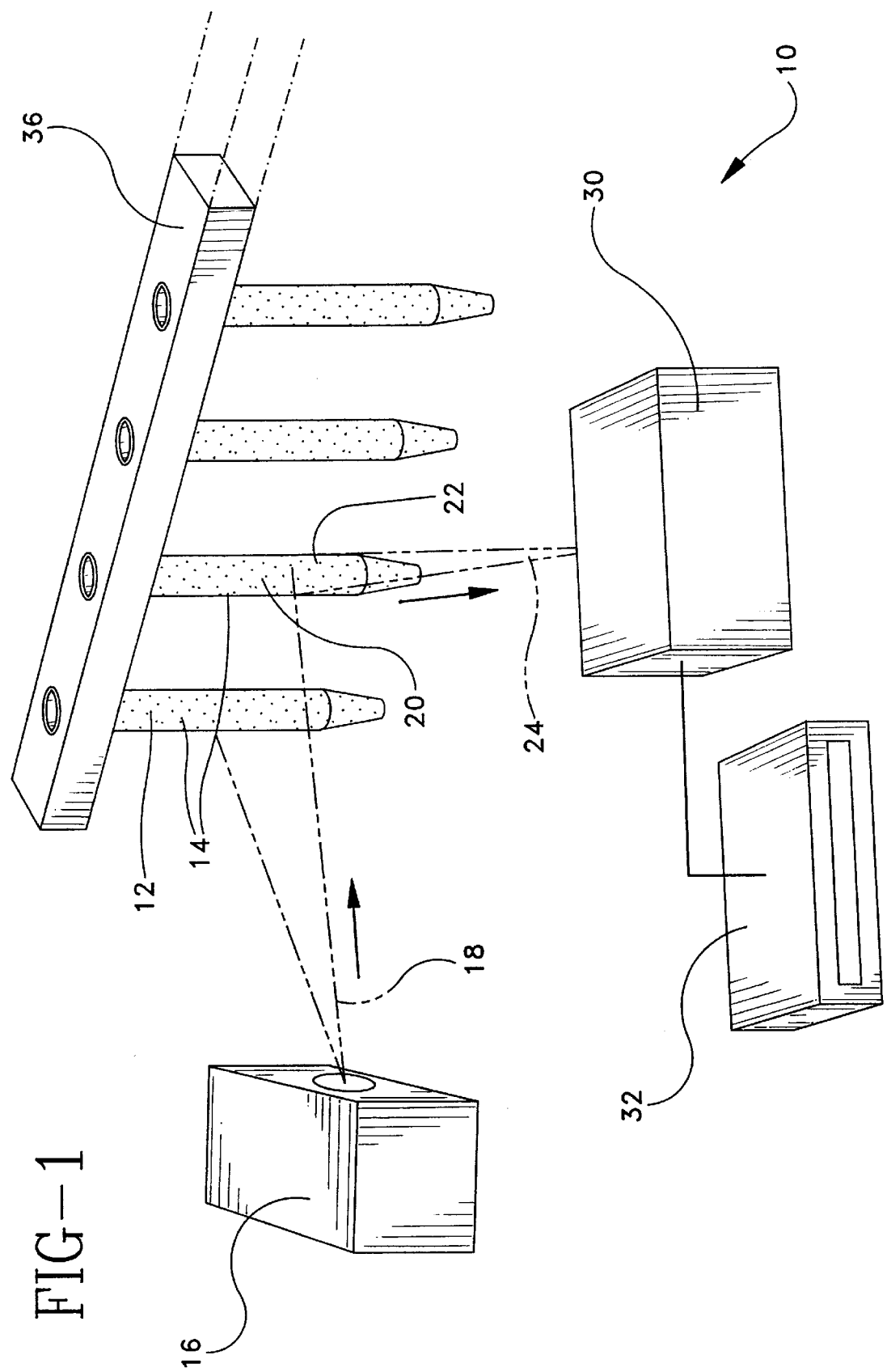
FIG. 1 is a schematic perspective view of a system using the preferred method of the present invention.

While this invention is satisfied by embodiments in many different forms, there are shown in the drawings and herein described in detail a preferred embodiment of the invention with the understanding that the present disclosure is to be considered exemplary of the principles of the invention and is not considered to limit the invention to the embodiment illustrated. The scope of the invention is measured by the appended claims and their equivalents.

Figure 2:
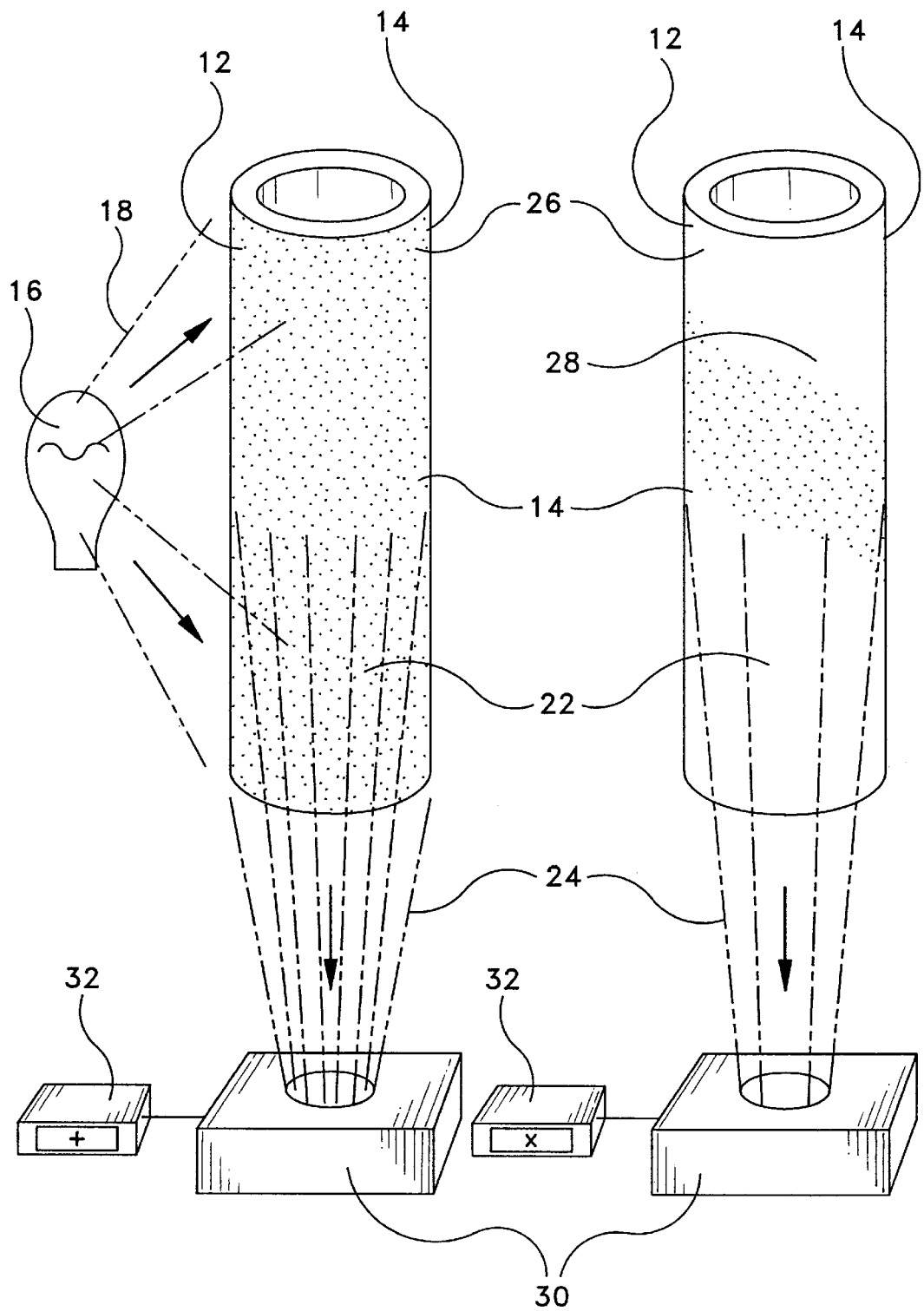
FIG. 2 is an enlarged schematic illustration of the irradiation and detection portions of the system of FIG. 1.
Figure 3:
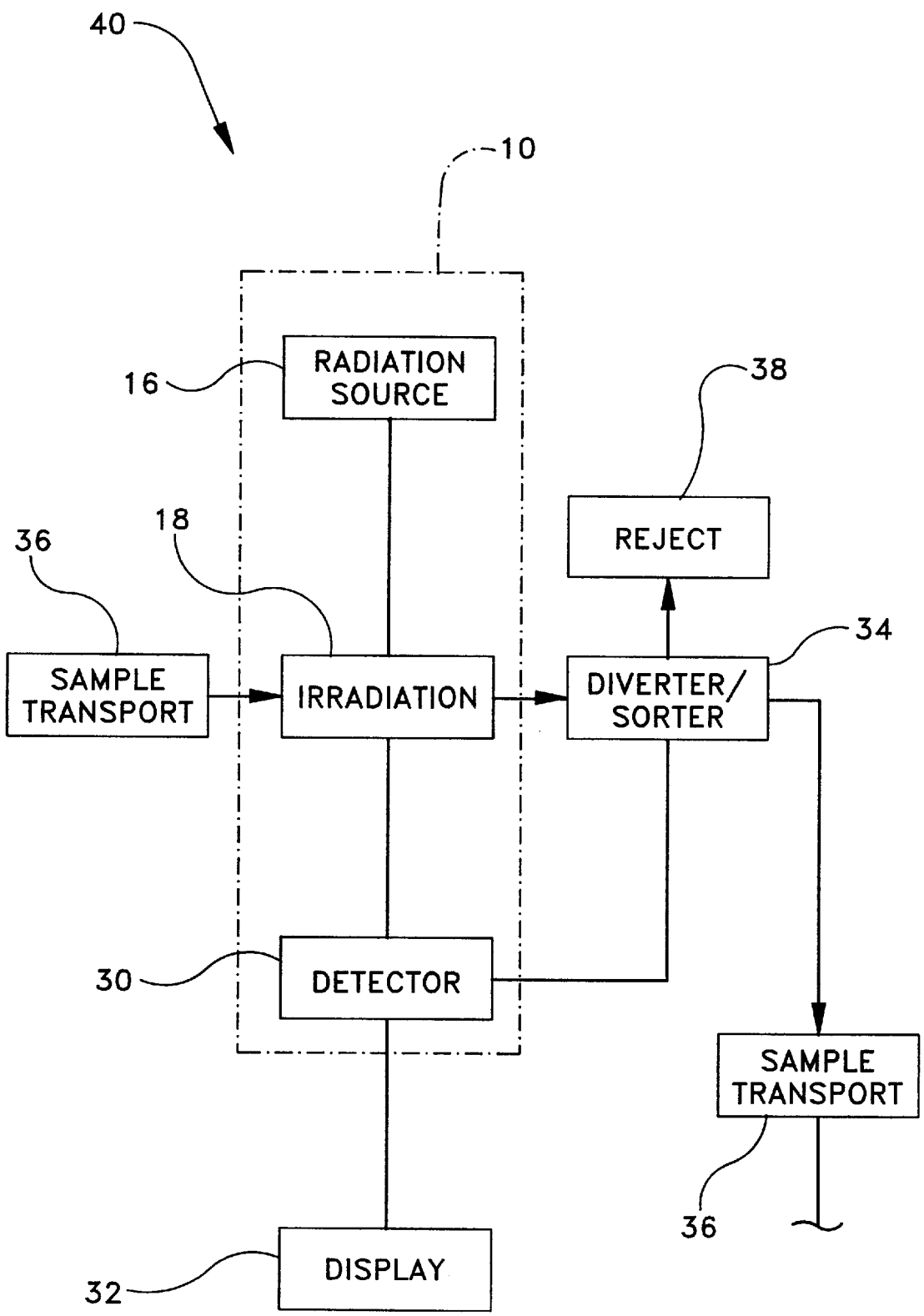
FIG. 3 is a block diagram of the system of the present invention as incorporated into an assembly line.

Referring to FIGS. 1–3, a preferred inspection system 10 of the present invention for determining a preselected degree of coverage of a polydimethylsiloxane lubricant on a surface 12 of a medical device 14 includes a source 16 of an electromagnetic radiation 18, preferably Ultraviolet (UV) radiation, for irradiation of a surface 12 of a medical device 14, such as a catheter 20 having thereon a coating 22 of polydimethylsiloxane. The use of the catheter as an example of medical device 14 is only intended to be illustrative of the principles of the invention and is not limitive of the invention to catheters. Application of the system to other medical devices, other objects or articles with a lubricant coating such as polydimethylsiloxane and the like is considered to be within the scope of the invention.

Polydimethylsiloxane coating 22 includes a fluorescent agent dissolved therein that provides a fluorescent emission 24 when the coating is irradiated by electromagnetic radiation 18. For the purpose of this description the polydimethyl siloxane or other lubricant with the fluorescent agent dissolved therein is said to be "fluorescenated".

System 10 may be used by an inspector to visually discriminate between device 14 having sufficient coating 22 to fulfill the manufacturer's specification and those that do not. The visual discrimination is schematically illustrated in FIG. 2, where fluorescent emission 24 allows visual differentiation between one catheter surface 26 with a uniform coating 22 and another catheter having only a partial coating 22 leaving a surface 28 that has no, or an uneven, coating.

System 10 preferably includes a detector 30 positioned to detect and respond to fluorescent emission 24 from the fluorescent agent in coating 22. Preferably, detector 30 has a maximum sensitivity to electromagnetic radiation having a wavelength between about 450 nm to about 520 nm. As a response, detector 30 generates a signal that preferably has a value proportional to the degree (coated area 26/uncoated area 28) of coverage of surface 12 by polydimethylsiloxane coating 22. Detector 30 preferably includes a capability to be adjusted to a preselected minimum threshold sensitivity value substantially corresponding to a preselected minimum degree of coverage of surface 12. Detector 30 preferably generates an output signal of the results of this comparison. Alternatively, detector 30 may include the capability to be adjusted to both a preselected minimum and maximum sensitivity values substantially corresponding to a preselected minimum and maximum degree of coverage of surface. In this alternative case, detector 30 preferably generates an output signal of the results of this comparison.

System 10 is useful in an assembly process line 40, as schematically illustrated in FIG. 1 and in the block diagram of FIG. 3. In this preferred application, the output signal from detector 30 may be displayed on a display 32, or more preferably, as is schematically shown in the block diagram, the detector output signal may be coupled to a diverter/sorter 34 to divert devices having other than the preselected degree of coating from a sample transport pathway 36 to a reject station 38. Alternatively, the detector output may be connected to an alarm, line shut-down or the like.

In order to be effective in this application, the fluorescent agent must have a degree of solubility in polydimethylsiloxane. Polydimethylsiloxane is an extremely hydrophobic material, and most fluorescent dyes are virtually insoluble it. As is reported above and in the cited references as an example, an individual medical device, such as the intravenous catheter, has only about 0.3 mg of polydimethylsiloxane of 12,500 cs. lubricant applied to it. Thus, given the size and surface area of the part, the coating of polydimethylsiloxane on the device surface is less than about $1 \times 10^{-3}$ mm thick. This fact, coupled with the physical properties of the polydimethylsiloxane, renders addition of even an intensely colored dye to the polydimethylsiloxane for visualization of the coating of little utility. Additionally, since a catheter is a medical device, addition of a substantial amount of a strongly colored dye is undesirable and subjects the device to additional approval steps. Further, most common dyes are only dispersible, not soluble, in polydimethylsiloxane. A trial where about 0.3 percent (wt./wt.) of an intensely colored violet dye, Calco oil violet ZIRS, available from BASF Corp., was only dispersed, not dissolved, in polydimethylsiloxane, did not allow an observer to easily determine if a uniform coating of polydimethylsiloxane was present on the catheter.

Preferred dyes for use in the system of the present invention include, but are not limited to, 7-diethylamino-4-trifluoromethyl-2H-1-benzopyran-2-one, commonly known as coumarin 481, 7-dimethylamino-4-trifluoromethyl-2H-1-benzopyran-2-one, commonly known as coumarin 485, mixtures thereof and the like. These dyes are made by Exiton, Dayton, Ohio and available from Eastman Chemical, Kingsport, Tenn. The preferred dyes are soluble in 12,500 cs. polydimethylsiloxane. The preferred dyes fluoresce strongly about 510 nm (yellow-green) when excited with the preferred UV radiation. A sufficiently strong fluorescent emission to allow visual discrimination between coated and uncoated surface is present when the preferred dyes are dissolved in polydimethylsiloxane at preferred concentrations between about 0.001 parts to about 0.01 parts in about 1,000 parts polydimethylsiloxane. Given the approximate 0.3 mg application of polydimethylsiloxane per catheter, the preferred concentration range results in an actual amount of the dye on an individual catheter between about 0.2 to about $1 \times 10^{-6}$ g. Both of the preferred dyes have been subjected to a battery of toxicity and mutagenicity tests at concentrations based on the actual delivery amount and at higher concentrations. The results of the toxicity and mutagenicity testing show no evidence of toxicity or mutagenicity for the preferred dyes. Other polydimethylsiloxane soluble fluorescent dyes that are demonstrated to be non-toxic and non-mutagenic would also be suitable and are within the scope of the present invention.

The fluorescent emission is sufficient to allow a visual differentiation, illustrated schematically in FIG. 2, between one catheter with a uniform coated area 26 and the other catheter with both coated area 26 and uncoated area 28. FIG. 2 also schematically illustrates two detectors 30, one showing an acceptable result for the catheter with uniform coating 26 and the other showing an unacceptable result for the catheter with uncoated area 28 greater than a preselected acceptable minimum value.

Preferably, electromagnetic radiation 18 from source 16 used to irradiate the surface of the devices coated with fluorescenated polydimethylsiloxane has a wavelength between about 300 nm to about 400 nm. A high pressure mercury vapor lamp has an emission spectrum with a wavelength maximum about 365 nm and is a preferred source of suitable UV radiation. Other sources having emission wavelength profiles different than the preferred high pressure mercury lamp would be suitable if their emission is passed through a monochrometer or the like to adjust their emission wavelength profile to generally approximate the emission profile of the preferred lamp. A suitable detector is a photometer having an adjustable threshold value and an adjustable sensitivity to fluorescent emission 24 having a wavelength between about 450 nm to about 520 nm. An L4T-1-4 Luminescence Scanner made by SICK Optic Electronics, Inc., (Germany) has been found to be suitable. Other photometric detectors having generally similar wavelength responses and adjustment features would also be suitable.

The method and system of the invention are substantially compatible with common line assembly speeds and space requirements. Use of the method and system of the invention provides a manufacturer of lubricated devices with a simple and efficient way to fulfill GMP requirements.

What is claimed is:

1. An inspection system for determining a preselected degree of coverage of a polydimethylsiloxane lubricant on a surface of a medical device comprising:

a source of electromagnetic radiation for irradiation of a surface of a medical device having thereon a coating of polydimethylsiloxane, said polydimethylsiloxane including a fluorescent agent at a concentration of between about $10^{-5}\%$ to about $10^{-6}\%$ dissolved therein, said irradiation being sufficient to induce a fluorescent emission from said fluorescent agent;

a detector having a maximum sensitivity to electromagnetic radiation having a wavelength between about 450 nm to about 520 nm, said detector being positioned to detect said fluorescent emission from said fluorescent agent in said polydimethylsiloxane and to generate a signal from said detector having a value proportional to the degree of coverage of the surface with the polydimethylsiloxane; and means for receiving the signal and comparing said value of the signal with a preselected value corresponding to a preselected degree of coverage of the surface of the medical device with the polydimethylsiloxane, said means further including a display to indicate the results of the comparison with the preselected value thereby providing a determination of said preselected degree of coverage.

2. The system of claim 1 wherein said fluorescent agent is selected from the group consisting of 7-diethylamino-4-trifluoromethyl-2H-1-benzopyran-2-one, 7-dimethylamino-4-trifluoromethyl-2H-1-benzopyran-2-one and mixtures thereof.

3. The system of claim 1 further comprising transport means for presenting a plurality of the medical devices to the radiation source and to the detector thereby enabling said system to monitor a plurality of the medical devices.

4. The system of claim 3 wherein said transport means further includes a sorting station responsive to said signal from the detector, said sorting station directing the medical devices having other than said preselected degree of coverage to a reject station.

* * * * *